United States Patent
Zambias et al.

[11] Patent Number: 5,807,754
[45] Date of Patent: Sep. 15, 1998

[54] COMBINATORIAL SYNTHESIS AND HIGH-THROUGHPUT SCREENING OF A REV-INHIBITING ARYLIDENEDIAMIDE ARRAY

[75] Inventors: Robert Zambias, Lexington, Mass.; David A. Bolten, Tinton Falls, N.J.; Joseph C. Hogan, Belmont, Mass.; Paul Furth, Waltham, Mass.; David Casebier, Hudson, Mass.; Cheng Tu, Cambridge, Mass.; Jaime E. Arenas, Lexington, Mass.

[73] Assignee: Arqule, Inc., Medford, Mass.

[21] Appl. No.: 439,577

[22] Filed: May 11, 1995
(Under 37 CFR 1.47)

[51] Int. Cl.$^6$ .......... G01N 33/543; G01N 33/551; C12Q 1/00
[52] U.S. Cl. .......... 436/518; 436/501; 436/524; 435/4
[58] Field of Search .......... 436/501, 518, 436/524; 435/5, 6, 235.1; 424/188.1, 208.1; 514/2

[56] References Cited

U.S. PATENT DOCUMENTS

| | | | |
|---|---|---|---|
| 5,288,514 | 2/1994 | Ellman | 427/2 |
| 5,306,631 | 4/1994 | Harrison et al. | 435/172.3 |
| 5,321,124 | 6/1994 | Haseltine et al. | 530/350 |

OTHER PUBLICATIONS

Jung et al. "Multiple Peptide Synthesis Methods and Their Applications"; Angewandte Chemie. Apr. 1992, vol. 31, No. 4, pp. 367–383.

Chemical abstract, vol. 120, No. 22. May 30, 1994 (Columbus, Ohio, USA), p. 658, col. 1, abstract No. 280277. Hogan, J.C. "Aminimide–containing molecules and materials as molecular recognition agents".

Chemical abstract, vol. 123, No. 23. Dec. 4, 1995 (Columbus, Ohio, USA), p. 909, column 2, the abstract No. 314023k. Hogan, J.C., "Systematic modular production of aminimide–and oxazolone–based molecules having selected properties".

*Primary Examiner*—Ponnathapura Achutamurthy
*Attorney, Agent, or Firm*—Pennie & Edmonds

[57] ABSTRACT

An n×m×p array of different chemical compounds, each having the following scaffold structure:

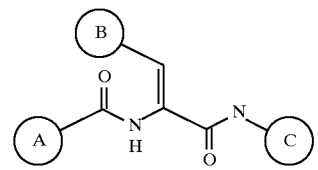

wherein n, m and p are integers, A, B and C are organic structural moieties representing diversity elements. The novel compounds present in this array are useful as inhibitors of binding of Rev protein to a Rev response element.

9 Claims, No Drawings

COMBINATORIAL SYNTHESIS AND HIGH-THROUGHPUT SCREENING OF A REV-INHIBITING ARYLIDENEDIAMIDE ARRAY

BACKGROUND OF THE INVENTION

The discovery of new molecules has traditionally focused in two broad areas, biologically active molecules, which are used as drugs for the treatment of life-threatening diseases, and new materials, which are used in commercial, especially high technological applications. In both areas, the strategy used to discover new molecules has involved two basic operations: (i) a more or less random choice of a molecular candidate, prepared either via chemical synthesis or isolated from natural sources, and (ii) the testing of the molecular candidate for the property or properties of interest. This discovery cycle is repeated indefinitely until a molecule possessing the desirable properties is located. In the majority of cases, the molecular types chosen for testing have belonged to rather narrowly defined chemical classes. For example, the discovery of new peptide hormones has involved work with peptides; the discovery of new therapeutic steroids has involved work with the steroid nucleus; the discovery of new surfaces to be used in the construction of computer chips or sensors has involved work with inorganic materials, etc. (for example, see R. Hirschmann, Angew. Chem., Int. Ed. in Engl. 1991, 30, 1278–1301). As a result, the discovery of new functional molecules, being ad hoc in nature and relying predominantly on serendipity, has been an extremely time-consuming, laborious, unpredictable, and costly enterprise.

A brief account of the strategies and tactics used in the discovery of new molecules is described below. The emphasis is on biologically interesting molecules. However, as discussed below, the technical problems encountered in the discovery of molecules and in the development of fabricated materials which can serve as new materials for high technological applications still limit the utility of most of theses methods.

Modern theories of biological activity state that biological activities, and therefore physiological states, are the result of molecular recognition events. For example, nucleotides can form complementary base pairs so that complementary single-stranded molecules hybridize resulting in double or triple-helical structures that appear to be involved in regulation of gene expression. In another example, a biologically active molecule, referred to as ligand, binds with another molecule, usually a macromolecule referred to as ligand-acceptor (e.g. a receptor or an enzyme), and this binding elicits a chain of molecular events which ultimately gives rise to a physiological state, e.g. normal cell growth and differentiation, abnormal cell growth leading to carcinogenesis, blood-pressure regulation, nerve-impulse-generation and -propagation, etc. The binding between ligand and ligand-acceptor is geometrically characteristic and extraordinarily specific, involving appropriate three dimensional structural arrangements and chemical interactions.

DESIGN AND SYNTHESIS OF MIMETICS OF BIOLOGICAL LIGANDS

A currently favored strategy for development of agents which can be used to treat diseases involves the discovery of forms of ligands of biological receptors, enzymes, or related macromolecules, which mimic such ligands and either boost (i.e., agonize) or suppress (i.e., antagonize) the activity of the ligand. The discovery of such desirable ligand forms has traditionally been carried out either by random screening of molecules (produced through chemical synthesis or isolated from natural sources, for example, see K. Nakanishi, Acta Pharm. Nord, 1992, 4, 319–328.), or by using a so-called "rational" approach involving identification of a lead-structure, usually the structure of the native ligand, and optimization of its properties through numerous cycles of structural redesign and biological testing (for example see Testa, B. & Kier, L. B. Med. Res. Rev. 1991, 11, 35–48 and Rotstein, S. H. & Murcko, M. J. Med. Chem. 1993, 36, 1700–1710.). Since most useful drugs have been discovered not through the "rational" approach but through the screening or randomly chosen compounds, a hybrid approach to drug discovery has recently emerged which is based on the use of combinatorial chemistry to construct huge libraries of randomly-built chemical structures which are screened for specific biological activities. (Brenner, S & Lerner, R. A. Proc. Natl. Acad. Sci. USA 1992, 89, 5381)

Most lead-structures which have been used in "rational" drug design are native polypeptide ligands of receptors or enzymes. The majority of polypeptide ligands, especially the small ones, are relatively unstable in physiological conditions, due to the tendency of the peptide bond to undergo facile hydrolysis in acidic media or in the presence of peptidases. Thus, such ligand, are decisively inferior in a pharmacokinetic sense to nonpeptidic compounds, and are not favored as drugs. An additional limitation of small peptides as drugs is their low affinity for ligand acceptors. This phenomenon is in sharp contrast to the affinity demonstrated by large, folded polypeptides, e.g., proteins, for specific acceptors, e.g., receptors or enzymes, which can be in the subnanomolar range. For peptides to become effective drugs, they must be transformed into nonpeptidic organic structures, i.e., peptide mimetics, which bind tightly, preferably in the nanomolar range, and can withstand the chemical and biochemical rigors of coexistence with biological fluids.

Despite numerous incremental advances in the art of peptidomimetic design, no general solution to the problem of converting a polypeptide-ligand structure to a peptidomimetic has been defined. At present, "rational" peptidomimetic design is done on an ad hoc basis. Using numerous redesign-synthesis-screening cycles, peptidic ligands belonging to a certain biochemical class have been converted by groups of organic chemists and pharmacologists to specific peptidomimetics; however, in the majority of cases the results in one biochemical area, e.g., peptidase inhibitor design using the enzyme substrate as a lead, cannot be transferred for use in another area, e.g., tyrosine-kinase inhibitor design using the kinase substrate as a lead.

In many cases, the peptidomimetics that result from a peptide structural lead using the "rational" approach comprise unnatural -amino acids. Many of these mimetics exhibit several of the troublesome features of native peptides (which also comprise alpha-amino acids) and are, thus, not favored for use as drugs. Recently, fundamental research on the use of nonpeptidic scaffolds, such as steroidal or sugar structures, to anchor specific receptor-binding groups in fixed geometric relationships have been described (see for example Hirschmann, R. et al. J. Am. Chem. Soc. 1992, 114, 9699–9701; Hirschmann, R. et al., J. Am. Chem. Soc., 1992, 114, 9217–9218); however, the success of this approach remains to be seen.

In an attempt to accelerate the identification of lead-structures, and also the identification of useful drug candidates through screening of randomly chosen compounds, researchers have developed automated methods for the generation of large combinatorial libraries of peptides and certain types of peptide mimetics, called "peptoids", which are screened for a desirable biological activity (see Gordon, E. M. et al. *J. Med Chem.* 1994, 37, 1385–1401). For example, the method of H. M. Geysen, (*Bioorg. Med. Chem. Letters,* 1993, 3, 397–404; *Proc. Natl. Acad Sci. USA* 1984, 81, 3998) employs a modification of Merrifield peptide synthesis, wherein the C-terminal amino acid residues of the peptides to be synthesized are linked to solid-support particles shaped as polyethylene pins; these pins are treated individually or collectively in sequence to introduce additional amino-acid residues forming the desired peptides. The peptides are then screened for activity without removing them from the pins. Houghton, (*Proc. Natl. Acad. Sci. USA* 1985, 82, 5131; Eichler, J. & Houghten, R. A. *Biochemistry,* 1993, 32, 11035–11041, and U.S. Pat. No. 4,631,211) utilizes individual polyethylene bags ("tea bags") containing C-terminal amino acids bound to a solid support. These are mixed and coupled with the requisite amino acids using solid phase synthesis techniques. The peptides produced are then recovered and tested individually. S. P. A: Fodor et al., (Science 1991, 251, 767) described light-directed, spatially addressable parallel-peptide synthesis on a silicon wafer to generate large arrays of addressable peptides that can be directly tested for binding lo biological targets. These workers have also developed recombinant DNA/genetic engineering methods for expressing huge peptide libraries on the surface of phages (Cwirla et al. *Proc. Natl. Acad. Sci. USA* 1990, 87, 6378; Barbas, et al. *Proc. Natl. Acad Sci. USA* 1991, 88, 7978–7982).

In another combinatorial approach, V. D. Huebner and D. V. Santi (U.S. Pat. No. 5,182,366) utilized functionalized polystyrene beads divided into portions each of which was acylated with a desired amino acid; the bead portions were mixed together, then divided into portions each of which was re-subjected to acylation with a second desirable amino acid producing dipeptides, using the techniques of solid phase peptide synthesis. By using this synthetic scheme, exponentially increasing numbers of peptides were produced in uniform amounts which were then separately screened for a biological activity of interest.

Zuckermann and coworkers (For examples, see Zuckermann, et al. *J. Med. Chem.* 1994, 37, 2678–2685 & Zuckermann, et al. *Int. J. Peptide Protein Res.* 1992, 91, 1) also have developed similar methods for the synthesis of peptide libraries and applied these methods to the automation of a modular synthetic chemistry for the production of libraries of N-alkyl glycine peptide derivatives, called "peptoids", which are screened for activity against a variety of biochemical targets. (See also, Symon et al., 1992, *Proc. Natl. Acad. Sci. USA* 89:9367). Encoded combinatorial chemical syntheses have been described recently (Brenner, S. & Lerner, R. A. *Proc. Natl. Acad. Sci. USA* 1992, 89, 5381; Barbas, C. F. et al. *Proc. Natl. Acad Sci. USA* 1992, 89, 4457–4461; see also Borchardt, A. & Still, W. C. *J. Am. Chem. Soc.* 1994, 116, 373–3741 Kerr, J. et al. *J Am. Chem. Soc.* 1993, 115, 2529–2531).

M. J. Kurth and his group (Chen, C. et al. *J. Am. Chem Soc.* 1994, 116, 2661–2662.) have applied organic synthetic strategies to develop non-peptide libraries synthesized using multi-step processes on a polymer support. Although the method demonstrates the utility of standard organic synthesis in the application and development of chemical libraries, the synthetic conditions are limited by compatibility with the solid support.

Although some means of quantification is needed to confirm this inhibitory action, conventional techniques include gel mobility shift assays and the like. These techniques are generally usable, but a need exists for improved assays and assaying methods for obtaining new compounds which possess this action.

SUMMARY OF THE INVENTION

The present invention relates to an n×m×p array of different chemical compounds, each having the following scaffold structure:

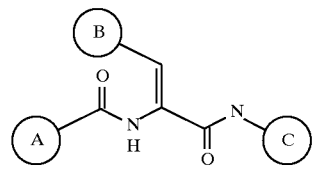

wherein n, a and p are integers A, B and C are diversity elements, and at least one of A, B or C is one of the following moieties:

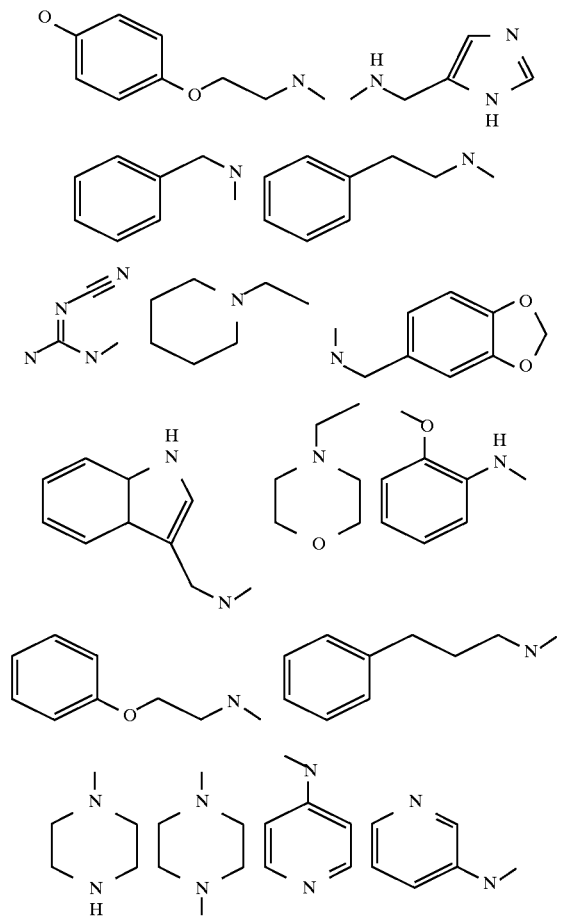

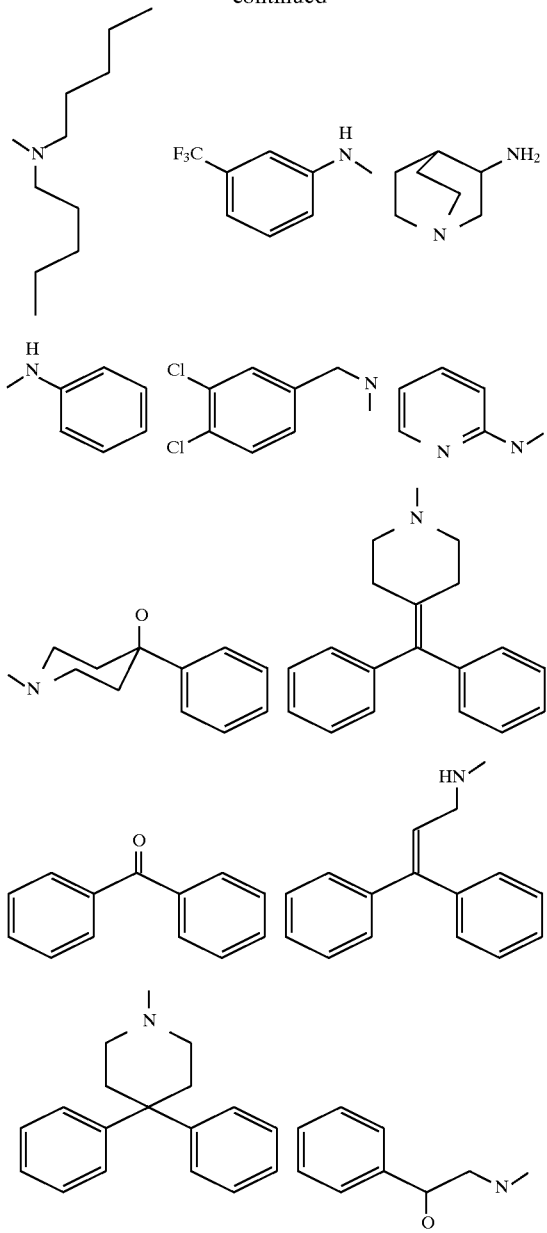
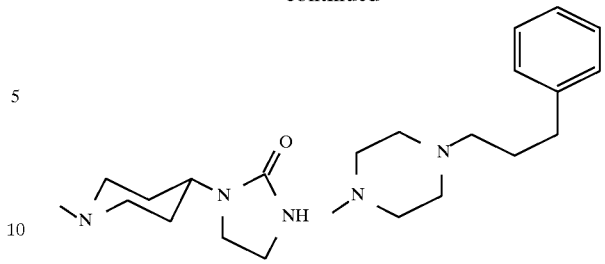

Preferred values for the integers n, m and p are n≧5, m≧2 and p≧1 with the product of n, m and p being greater than 25. In a further preferred embodiment n≧8, m≧12 and p≧2. The most preferred array includes 10,240 compounds with n=8, m=12 and p=40, wherein A is selected from phenyl, m-methoxyphenyl, 2-naphthyl, 2-thiophenyl, α,α,α-trifluoro-p-toluyl, 2,4-dichlorophenyl, p-toluyl, or m-toluyl; B is selected from 2,4-difluorophenyl, 2-fluorophenyl, 3-fluorophenyl, 4-fluorophenyl, α,α,α-trifluoro-m-toluyl, α,α,α-trifluoro-p-toluyl, o-toluyl, m-toluyl, p-toluyl, 4-ethylphenyl, phenyl, 4-biphenylyl, 1-naphthyl, 4-(trifluoromethoxy)phenyl, 3-(phenoxy)phenyl, 2-thiophenyl, 3-thiophenyl, 3,5-difluorophenyl, 3-pyridinyl, 4-pyridinyl, 4-chlorophenyl, 3-quinolinyl, 4-quinolinyl, 2-furyl, 3-furyl, or 5-methylfur-2-yl; and C is selected from (2-tetrahydrofuryl)methyl, isobutyl, (+)-sec-butyl, cyclobutyl, cyclohexyl, 1-ethylpropyl, 2-hydroxyethyl, (+)-hydroxypropyl, 2-hydroxyphenethyl, (−)-ephidryl, 1-hydroxy-4-methylpent-2-yl, pentamethylenyl, 3-benzylpentamethylenyl, 2,2'-bis-ethylether, 4-phenylbut-2-yl, 3-phenylpropyl, benzyl, phenethyl, 1,2,3,4-terahydronaphthyl, 2-(p-toluyl)ethyl, diphenylmethyl, 2,2-diphenylethyl, 1-indanyl, 2-phenethyl, (1-naphthyl)methyl, (2-furyl)methyl, 3,4-dimethoxyphenethyl, N-ethylcarboxy-2,2'-aminodiethyl, 2-(N-pyrrolidinyl)ethyl, N-phenyl-2,2'-aminodiethyl, 1-benzyl-4-piperidinyl, N-piperonyl-2,2'-aminodiethyl, 3-(4-morpholinyl)propyl, 3(1-imidazolyl)propyl, 3-(N,N-dimethylamino)propyl, N-(α,α,α-trifluoro-m-toluyl)-2,2'-aminodiethyl, (2-pyridinyl)methyl, 2-(1-piperidinyl)ethyl, or N-methyl-2,2'-aminodiethyl.

The invention is further directed to the compounds from the arrays described above. Preferred embodiments thereof concern compounds having the scaffold structure described above, wherein A, B and C are one of the following combinations of diversity elements:

| A | B | C |
|---|---|---|
| 2,4-dichlorophenyl | phenyl | cyclohexyl |
| 2-naphthyl | ααα-trifluoro-m-toluyl | 1,2,3,4-tetrahydronaphth-1-yl |
| 2-naphthyl | ααα-trifluoro-m-toluyl | diphenylmethyl |
| 2,4-dichlorophenyl | ααα-trifluoro-m-toluyl | diphenylmethyl |
| 2-naphthyl | ααα-trifluoro-m-toluyl | 2-(p-toluyl)ethyl |
| 2-naphthyl | ααα-trifluoro-m-toluyl | diphenylmethyl |
| p-toluyl | 2,4-difluorophenyl | 2-hydroxyphenethyl |
| 2-naphthyl | 3-quinolinyl | (1-naphthyl)methyl |
| 2-naphthyl | ααα-trifluoro-m-toluyl | 4-phenylbut-2-yl |
| 2,4-dichlorophenyl | 4-biphenylyl | diphenylmethyl |
| 2-naphthyl | 4-(trifluoromethoxy)phenyl | diphenylmethyl |
| 2-naphthyl | ααα-trifluoro-p-toluyl | 2,2-diphenylethyl |
| 2-naphthyl | ααα-trifluoro-p-toluyl | 1,2,3,4-tetrahydronaphth-1-yl |
| 2,4-dichlorophenyl | 3-(phenoxy)phenyl | 2-(p-toluyl)ethyl |
| p-toluyl | 2-chlorophenyl | 3-(4-morpholinyl)propyl |
| 2-naphthyl | 2,4-dichlorophneyl | 2-hydroxyphenethyl |

-continued

| A | B | C |
|---|---|---|
| 2-naphthyl | α,α,α-trifluoro-m-toluyl | 3-benzylpentamethylenyl |
| α,α,α-trifluoro-p-toluyl | α,α,α-trifluoro-p-toluyl | 2-(p-toluyl)ethyl |
| α,α,α-trifluoro-p-toluyl | α,α,α-trifluoro-p-toluyl | 1,2,3,4-tetrahydronaphth-1-yl |
| α,α,α-trifluoro-p-toluyl | 3-(phenoxy)phenyl | diphenylmethyl |
| 2,4-dichlorophenyl | 4-biphenylyl | 2-(p-toluyl)ethyl |
| 2-naphthyl | m-anisyl | diphenylmethyl |
| 2-naphthyl | α,α,α-trifluoro-m-toluyl | (1-naphthyl)methyl |
| 2,4-dichlorophenyl | 4-biphenylyl | benzyl |
| 2,4-dichlorophenyl | 3,5-difluorophenyl | 2,2-diphenylethyl |
| 2-naphthyl | α,α,α-trifluoro-m-toluyl | 1-hydroxy-4-methylpent-2-yl |
| 2-naphthyl | 4-(trifluoromethoxy)phenyl | 1,2,3,4-tetrahydronaphth-1-yl |
| 2-naphthyl | α,α,α-trifluoro-m-toluyl | 2,2-diphenylethyl |
| 2-naphthyl | α,α,α-trifluoro-m-toluyl | pent-3-yl |
| 2,4-dichlorophenyl | α,α,α-trifluoro-m-toluyl | 2,2-diphenylethyl |
| 2-naphthyl | α,α,α-trifluoro-m-toluyl | diphenylmethyl |
| 2-naphthyl | α,α,α-trifluoro-m-toluyl | 2-furyl |
| 2-naphthyl | 2,4-difluorophenyl | (1-naphthyl)methyl |
| 2-naphthyl | 3-chlorophenyl | diphenylmethyl |
| 2-naphthyl | α,α,α-trifluoro-p-toluyl | 1-indanyl |
| 2-naphthyl | α,α,α-trifluoro-m-toluyl | 1-indanyl |
| α,α,α-trifluoro-p-toluyl | 4-chlorophenyl | 1,2,3,4-tetrahydronaphth-1-yl |
| 2,4-dichlorophenyl | 4-biphenylyl | 1,2,3,4-tetrahydronaphth-1-yl |
| 2-naphthyl | m-anisyl | phenethyl |
| phenyl | 2-fluorophenyl | 3-pyridinyl |
| 2,4-dichlorophenyl | 3,5-difluorophenyl | 3-pyridinyl |
| 2-naphthyl | 2,4-dichlorophenyl | 3-pyridinyl |
| 2-naphthyl | α,α,α-trifluoro-p-toluyl | 3-benzylpentamethylenyl |
| 2-naphthyl | α,α,α-trifluoro-p-toluyl | 3-phenylpropyl |
| α,α,α-trifluoro-p-toluyl | α,α,α-trifluoro-p-toluyl | N-phenyl-2,2'-aminodiethyl |
| 2,4-dichlorophenyl | 4-biphenyl | phenethyl |
| 2,4-dichlorophenyl | 4-biphenyl | 1-indanyl |
| 2-naphthyl | 4-fluorophenyl | 2,2-diphenylethyl |
| α,α,α-trifluoro-p-toluyl | 3-(phenoxy)phenyl | 1,2,3,4-tetrahydronaphth-1-yl |
| 2-naphthyl | α,α,α-trifluoro-m-toluyl | 1,2,3,4-tetrahydronaphth-1-yl |
| 2,4-dichlorophenyl | α,α,α-trifluoro-p-toluyl | N-(α,α,α-trifluoro-m-toluyl)-2,2'-aminodiethyl |
| p-toluyl | 2-chlorophenyl | (1-naphthyl)methyl |
| α,α,α-trifluoro-p-toluyl | 3-(phenoxy)phenyl | N-phenyl-2,2'-aminodiethyl |
| 2,4-dichlorophenyl | 4-biphenyl | (1-naphthyl)methyl |
| 2,4-dichlorophenyl | α,α,α-trifluoro-m-toluyl | 1,2,3,4-tetrahydronaphth-1-yl |

Further details concerning the arrays of the invention and methods of making the same can also be found in copending application Ser. No. 08/375,838 filed Jan. 20, 1995 now U.S. Pat. No. 5,712,171, the entire content of which is expressly incorporated herein by reference thereto.

DEFINITIONS

This invention disclose a system for the design, synthesis & use of logically arranged collections of synthetic product molecules called "molecular constructs" from structural elements in such a manner that the collection of molecular constructs possesses a constant structural element and a variable structural element. The definitions are shown below.

A "construct" is a molecule which is a member of a collection of molecules containing a common constant structural element and a common variable structural element.

An "array" is a logical positional ordering of molecular constructs in Cartesian coordinates.

A "bond" or "chemical bond" is used to describe a group of electrons that is shared between two atoms. This term also denotes an ionic, covalent or other attractive force between two atoms.

A "building block" is any molecule useful in the assembly of a molecular construct.

The terms "fragment" or "structural diversity element" refer to the common variable structural element of a molecular construct.

The "molecular core" is the common constant structural element of a molecular construct.

A "spatial address" is a position in the array defined by unique Cartesian coordinates.

A "sub-array" is a set of spatial addresses within a given array containing those molecular constructs having a common molecular core and differ from each other by 0 (zero) or 1 (one) change in a fragment.

A "relative address" refers to a location within the array or sub array comparable to any selected address, and differing by 0 (zero) or only 1 (one) change in the common variable structural element.

Inhibition and High-Throughput Screening of HIV Proteins

Tho human immunodeficiency virus (HIV) has been implicated as the causative agent of acquired immune deficiency syndrome (AIDS) (Popovic.; et al., Science, 198, 1984 497). The RNA genome of the HIV retrovirus encodes an aspartic protease known as the HIV-1 protease (Kramer, R. A.; et al., Science, 1986, 231, 1580). This protease is required for maturation and proliferation of the infectious virion. The role of the HIV-1 protease is to cleave viral precursor proteins, in particular the Gag and Pol precursor proteins, into their active forms (Darke, P. L.; et al., Biochem. Biophys. Res. Comm, 1988, 156, 297). To date, numerous inhibitors of HIV-1 protease have been reported in the literature (Wlodawer, A.; Erickson, J. W., Annu. Rev. Biochem., 1993, 62, 543).

Additionally, the RNA genome of the HIV retrovirus encodes for two viral regulatory proteins, Tat and Rev. Tat is a transcriptional activator, and Rev is a post-transcriptional protein that binds to a specific sequence of ribonucleic acid, the Rev Repsonse element (RRE). This action raises the intracellular concentrations of gag-pol and cnv messenger RNA (mRNA), thereby perpetuating the viral replication cycle. (for a review of this material see Green, M. R. *AIDS Res. Rev.* 1993, 3, 41–55.) Research in the field has shown that introduction of analogous sequences of nucleic acids to the mRNA within the RRE show a decrease in the concentration of Rev protein (Matsukura, M.; et al. *Proc. Natl. Acad Sci. USA* 1989, 86, 4244–4248). Another valuable insight was the discovery that small molecules can provide this inhibitory action. Aminoglycoside antibiotics inhibit protein synthesis at what is believed to be at the level of ribosomal RNA (reviewed by Cundliffe, E. in *The Ribosome: Structure, Function and Evolution* Hill, W. E.; et al., eds. (American Society for Microbiology, Washington, D. C.) 1990, pp 479–490) Furthermore it was found that aminoglycoside antibiotics block the binding of Rev to RRE, inhibit Rev function and viral production in vivo (Zapp, M. L.; Stern, S.; Green, M. R. *Cell* 1993, 75, 969–978).

An "operator" is a simultaneous and/or concurrent change in the condition of at least two spatial addresses in individual cells residing in an array or a sub-array that results in a structural change at least one molecular construct in the array. In particular, an operator in terms of this invention can be the reaction of at least one site on the molecular core capable of becoming or providing attachment for a structural diversity element, to add or change a structural motif thereon. Other operators which can be performed according to the patent include but are not limited to: addition of reagents or solvents; quality control protocols such as gas chromatography, high performance liquid chromatography, mass spectrometry, infrared spectroscopy, ultraviolet spectroscopy, nuclear magnetic resonance spectroscopy, fluorescence spectroscopy, melting point, mass balance, combustion analysis and thin layer chromatography; biological and enzymological assays such as ELISA, spectroscopic inhibition assays, disc assays and binding affinity assays; mechanical motions or manipulations; passage of time which includes resting & evaporation; heating and cooling; iteration of previous steps in a synthesis; dilution and dispensation of products in a form suitable for the design purpose.

The protein herein referred to as "Rev" or "the Rev Protein" means an HIV regulatory protein that is critical for key steps in the life cycle of the Human Immunodeficiency Virus (HIV).

DETAILED DESCRIPTION OF THE INVENTION

This invention is directed to an n×m×p array of different chemical compounds wherein each of these compounds has at least one structural diversity element selected from among the following moieties:

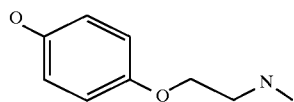

-continued

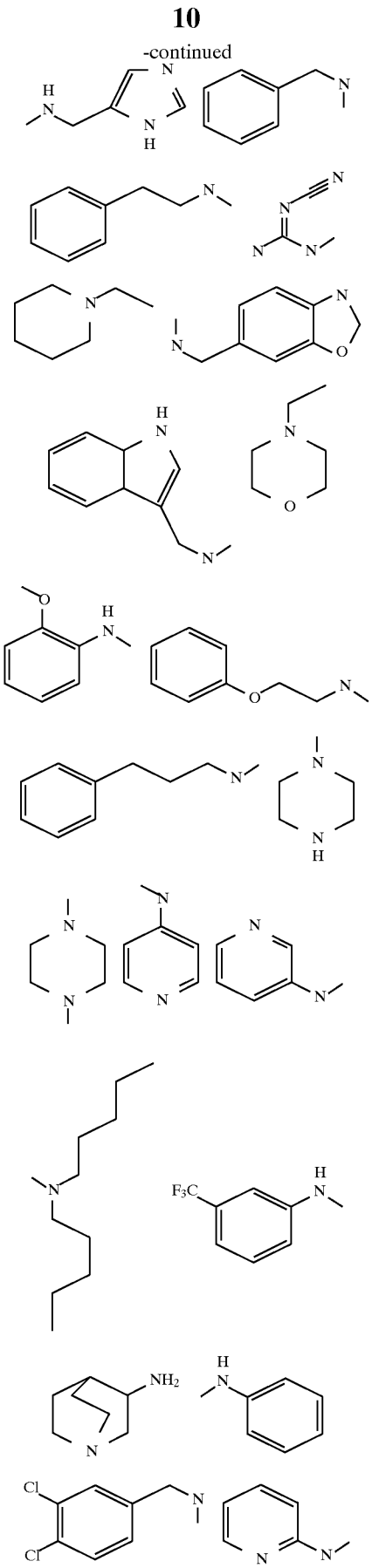

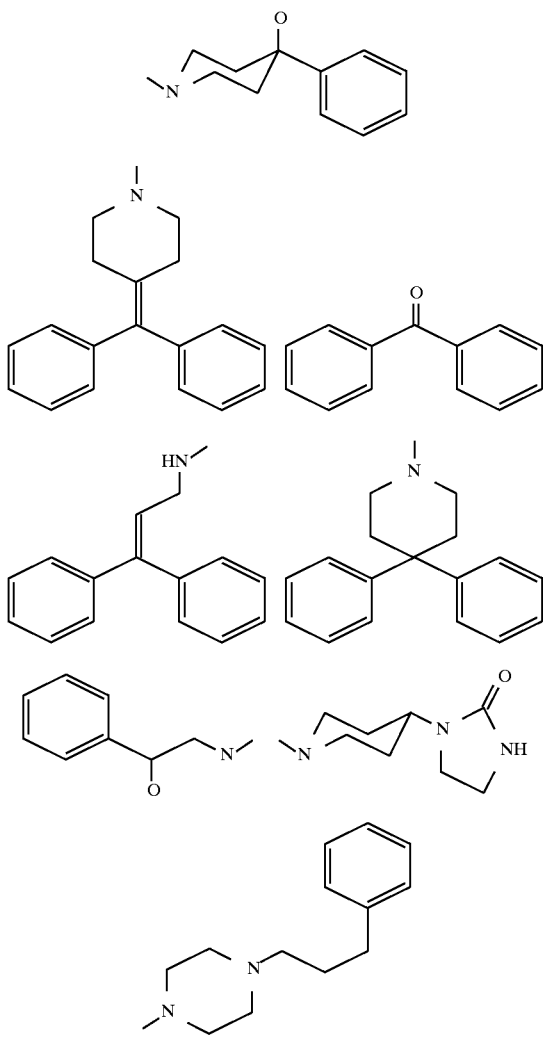

This invention pertains to the logical layout, construction and testing of an array of chemical compounds blocking the binding of Rev Protein to the Rev Response Element, in which the desired properties of the compound can be measured and correlated to specific ordered changes in the fragments use to construct them. The array is ordered in such a fashion as to expedite assembly, to maximize the informational content derived from the testing and to facilitate the rapid extraction of that data from the testing process. This array and the coupled high-throughput screening has great utility in accelerating the development of compounds having the optimal properties for the inhibition of HIV replication.

An application of this invention is the rapid determination and optimization or candidates for blocking the binding of Rev to RRE. The array is screened and the optimal candidates are chosen. Thus in one light the invention is the most powerful tool to date for the rapid screening and testing of compounds for IND candidacy against this target. This method is facilitated by virtue of selecting fragments based solely upon their ability to participate in the process of assembly into the arylidenediamide core and then the entirety of the library is screened for inhibition of the Rev-RRE binding.

The logically arranged array of the present invention is fundamentally different from all known prior art. Testing of these arrays automatically results in the generation of complete relational structural information such that a positive result provides: (1) information on a compound within any given spatial address; (2) simultaneous juxtaposition of this information upon a set of systematically structural congeners; (3) the ability to extract relational structural information from negative results in the presence of positive results. Thus by analyzing the percent inhibition and correlating this information to the known structural components at each address, a valid Structure-Activity Relationship (SAR) is rapidly established. All known prior art is universally directed toward the maximization of structural diversity. By definition this has excluded the acquisition or maximal data. In these cases, the relationship between individual structural variations and any resulting changes in a measurable property of the compounds can not be directly obtained from these testing results. Methods in the prior art universally require extensive further experimentation to elucidate any relational information in a process which is costly, time consuming and one in which success is difficult to predict.

This array is constructed from the arylidenediamide core shown below. The core candidate was selected so that the scaffold a) presents attachment points for at least two structural diversity elements; b) is able to present these structural diversity elements in controlled, varying spatial arrangements; c) can be constricted in a rapid concerted fashion.

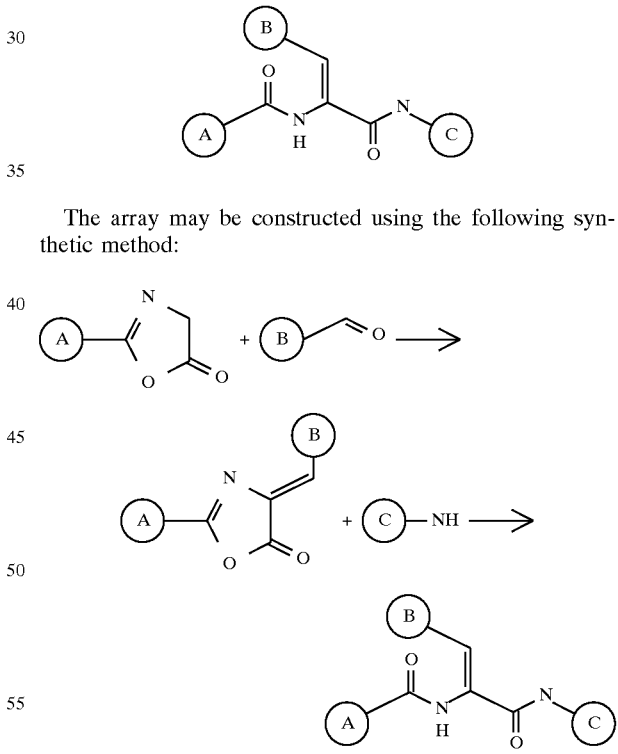

The array may be constructed using the following synthetic method:

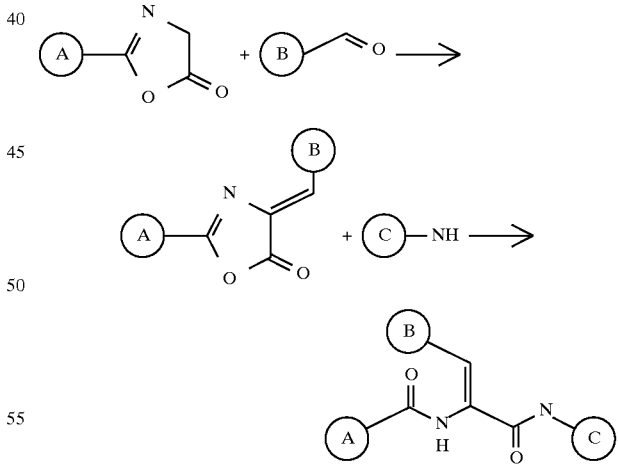

The substituents A, B, & C on the molecular core are structural diversity elements which may be the same or different and each represents straight or branched chain alkyl, carbocyclic aryl and substituted or heterocyclic derivatives thereof.

As used herein, the phrase linear chain or branched chained alkyl groups means any substituted or unsubstituted acyclic carbon-containing compounds, including alkanes, alkenes and alkynes. Alkyl groups having up to 30 carbon atoms are preferred. Examples of alkyl groups include lower alkyl, for example, methyl, ethyl, n-propyl, iso-propyl, n-butyl, iso-butyl or tert-butyl; upper alkyl, for example, octyl, nonyl, decyl, and the like; lower alkylene, for example, ethylene, propylene, propyldiene, butylene, butyldiene; upper alkenyl such as 1-decene, 1-nonene, 2,6-dimethyl-5-octenyl, 6-ethyl-5-octenyl or heptenyl, and the like; alkynyl such as 1-ethynyl, 2-butynyl, 1-pentynyl and the like. The ordinary skilled artisan is familiar with numerous linear and branched alkyl groups, which are within the scope of the present invention.

In addition, such alkyl group may also contain various substituents in which one or more hydrogen atoms has been replaced by a functional group. Functional groups include but are not limited to tertiary amine, amide, ester, ether, and halogen (fluorine, chlorine, bromine and iodine), to mention but a few. Specific substituted alkyl groups can be, for example, alkoxy such as methoxy, ethoxy, butoxy, pentoxy and the like, dimethylamino, diethylamino, cyclopentylmethylamino, benzylmethylamino, dibenzylamino, and the like; formamido, acetamido, butanamido, and the like, methoxycarbonyl, ethoxycarbonyl or the like, or dimethyl or diethyl ether groups or the like.

As used herein, substituted and unsubstituted carbocyclic groups of up to about 20 carbon atoms means cyclic carbon-containing compounds, including but not limited to cyclopentyl, cyclohexyl, cycloheptyl, adamantyl, and the like. Such cyclic groups may also contain various substituents in which one or more hydrogen atoms has been replaced by a functional group. Such functional groups include those described above, and lower alkyl groups as described above. The cyclic groups of the invention may further comprise a hetero-atom. For example, in a specific embodiment, structural diversity element C is N,N-dimethyl aminoethyl As used herein, substituted and unsubstituted aryl groups means a hydrocarbon ring bearing a system of conjugated double bonds, usually comprising (4p−2) pi bond electrons, where p is an integer equal to or greater than 1. Examples of aryl groups include, but are not limited to, phenyl, naphthyl, anisyl, toluyl, xylenyl and the like. According to the present invention, aryl also includes aryloxy, aralkyl, aralkyloxy and heteroaryl groups, e.g., pyrimidine, morpholine, piperazine, piperidine, benzoic acid, toluene or thiophene and the like. These aryl groups may also be substituted with any number of a variety of functional groups. In addition to the functional groups described above in connection with substituted alkyl groups and carbocyclic groups, functional groups on the aryl groups can be nitro groups.

As mentioned above, structural diversity elements can also represent any combination of alkyl, carbocyclic or aryl groups; for example, 1-cyclohexylpropyl, benzylcyclohexylmethyl, 2-cyclohexyl-propyl, 2,2-methylcyclohexylpropyl, 2,2-methylphenylpropyl, 2,2-methylphenylbutyl, and the like. The structural diversity element may also be a chemical bond or a connecting group that includes a terminal carbon atom for attachment to the quaternary nitrogen and may be different in adjacent n units.

In a preferred embodiment of the invention the structural diversity element "A" is derived from the set of 2-naphthyl, α,α,α-trifluoro-p-toluyl, 2,4-dichlorophenyl, and p-toluyl. In another preferred embodiment of the invention, the structural diversity element "B" is dercived from the set of α,α, α-trifluoro-m-toluyl, α,α,α-trifluoro-p-toluyl, and 4-biphenylyl. In still another preferred embodiment of the invention the structural diversity element "C" is derived from the act of 1,2,3,4-tetrahydronaphthyl, 2-(p-toluyl) ethyl, diphenylmethyl, 2,2-diphenylethyl, and (1-naphthyl) methyl. In a highly preferred embodiment of the invention, these aforementioned sets are employed in combination such that the molecule of interest possesses structural diversity elements drawn from all three sets.

The following experimental procedure is meant to exemplify but one embodiment of the present invention and are not intended to limit the invention thereto.

EXAMPLE

A 10,240-component array is synthesized and assayed according to the teaching of the invention, from eight oxazolones (Building Block A), 32 aldehydes (Building Block B), and 40 amines (Building Block C).

Tetrahydrofuran (THF) solutions of the building blocks are prepared to concentrations of 250 mM in "A" (oxazolone), 250 mM in "B" (aldehyde), and 500 mM in "C" (amine). Sufficient volumes of each solution are prepared to allow for the production of one row of reaction plates (Px, where x=1–128 for AN 1001). A reaction plate contains 80 spatial addresses each (8×10) and a row Contain 16 reaction plates. The entire array consists of 8 rows of these reaction plates which are recycled 16 at a time to complete production of the array. The initial cycle's first operator is spatial delivery of 200 ul (1 cq., 50 uMoles) of the "A" building block solution starting at P1 and ending at P16. The second operator is spatial delivery of 200 ul (1 eq., 50 uMoles) of the "B" Building Blocks to the same reaction plates The third operator is addition to the same reaction plates of 50 uL of a 1M (1 eq., 50 uMoles) solution of triethylamine in THF to all the spatial addresses that "A" and "B" building Blocks were added. The forth operator is placement of the reaction blocks on an agitator at 60 degrees centigrade for 1.5 hrs. The fifth operator is spatial addition of 100 ul (1 cq., 50 uMoles) of the "C" building block solutions. The sixth operator is addition of 200 uL of THF to an the spatial addresses in the row or cycle. The seventh operator allows the reaction plates Lo stand at 25 degrees centigrade for 16 hrs. enabling evaporation of THF and completion of the synthesis of the molecular constructs. The following operators are then applied to distribute and reformat the molecular constructs for delivery and quality control. Heat the reaction plates to 60 degrees centigrade for 10 minutes and add 400 ul of dimethylsulfoxide (DMSO) to dissolve the molecular constructs (operator 8 ). Remove the solution from the reaction plates and place in a plastic microtiter plates in a spatial manner (operator 9). Spatially wash the reaction plates (each address) with 4 times 325 uL of DMSO and place in the same microtiter plates (operator 10). This affords 29.4 mM solutions of the molecular constructs in DMSO ready for further spatial distribution. Remove a 10 uL aliquot following a unique address pattern layout from each microtiter plate for quality control (operator 11). Spatially reformat these aliquots, dilute with 300 uL of acetonitrile and subject these samples to analysis by High Performance Liquid Chromatography and Mass Spectrometry for quality control of the molecular constructs in the each microtiter plate (operator 12). The above cycles and operators are repeated 7 more times to finish production and quality controlled validation of the array, AN 1001.

The array was assayed in parallel at 6 ug/mL in reaction mixtures containing recombinant Rev protein, synthetic 32P-labelled RRE RNA, and a non-specific competitor RNA. The reaction is then filtered through nitrocellulose filters and washed with a low salt binding buffer. Rev-RRE complexes are retained in the filter while the unbound RRE filters through. Rev-RRE complexes retained in the filter are then quantified by scintillation counting. The percentage of inhibition is calculated according to the formula:

$$\%inh = (1-(CPM1/CPM0)) \times 100$$

where CPM1 is the activity obtained in the presence of the drug and CPM0 is the average activity in the absence of the drug. Compounds of interest as potential Rev-RRE inhibitors are expected to cause at least 50% inhibition and not to precipitate at concentrations of 6 ug/mL or lower. Cursory examination of these assay results showed that of 10,240 compounds, 752 of these inhibited the binding of Rev to RRE at a value or greater than 50%. Raising the criterion of interest to 90% inhibition of complex formation afforded a set of 55 compounds which were examined for common functionality. These 55 compounds and their inhibition values are listed in the following table, where A, B, and C are the structural diversity elements of the scaffold:

| % inh | A | B | C |
|---|---|---|---|
| 98 | 2,4-dichlorophenyl | phenyl | cyclohexyl |
| 97 | 2-naphthyl | α,α,α-trifluoro-m-toluyl | 1,2,3,4-tetrahydronaphth-1-yl |
| 96 | 2-naphthyl | α,α,α-trifluoro-m-toluyl | diphenylmethyl |
| 96 | 2,4-dichlorophenyl | α,α,α-trifluoro-m-toluyl | diphenylmethy |
| 96 | 2-naphthyl | α,α,α-trifluoro-m-toluyl | 2-(p-toluyl)ethyl |
| 96 | 2-naphthyl | α,α,α-trifluoro-p-toluyl | diphenylmethyl |
| 96 | p-toluyl | 2,4-difluorophenyl | 2-hydroxyphenethyl |
| 96 | 2-naphthyl | 3-quinolinyl | (1-naphthy))methyl |
| 96 | 2-naphthyl | α,α,α-trifluoro-p-toluyl | 4-phenylbut-2-yl |
| 96 | 2,4-dichlorophenyl | 4-biphenylyl | diphenylmethyl |
| 96 | 2-naphthyl | 4-(trifluoromethoxy)phenyl | diphenylmethyl |
| 95 | 2-naphthyl | α,α,α-trifluoro-p-toluyl | 2,2-diphenylethyl |
| 95 | 2-naphthyl | α,α,α-trifluoro-p-toluyl | 1,2,3,4-tetrahydronaphth-1-yl |
| 95 | 2,4-dichlorophenyl | 3-(phenoxy)phenyl | 2-(p-toluyl)ethyl |
| 95 | p-toluyl | 2-chlorophenyl | 3-(4-morpholinyl)propyl |
| 95 | 2-naphthyl | 2,4-dichlorophenyl | 2-hydroxyphenethyl |
| 95 | 2-naphthyl | α,α,α-trifluoro-m-toluyl | 3-benzylpentamethylenyl |
| 95 | α,α,α-trifluoro-p-toluyl | α,α,α-trifluoro-p-toluyl | 2-(p-toluyl)ethyl |
| 94 | α,α,α-trifluoro-p-toluyl | α,α,α-trifluoro-p-toluyl | 1,2,3,4-tetrahydronaphth-1-yl |
| 94 | α,α,α-trifluoro-p-toluyl | 3-(phenoxy)phenyl | diphenylmethyl |
| 94 | 2,4-dichlorophenyl | 4-biphenylyl | 2-(p-toluyl)ethyl |
| 94 | 2-naphthyl | m-anisyl | diphenylmethyl |
| 94 | 2-naphthyl | α,α,α-trifluoro-m-toluyl | (1-naphthyl)methyl |
| 94 | 2,4-dichlorophenyl | 4-biphenylyl | benzyl |
| 94 | 2,4-dichiorophenyl | 3,5-difluorophenyl | 2,2-diphenylethyl |
| 94 | 2-naphthyl | α,α,α-trifluoro-m-toluyl | 1-hydroxy-4-methylpent-2-yl |
| 94 | 2-naphthyl | 4-(trifluoromethoxy)phenyl | 1,2,3,4-tetrahydronaphth-1-yl |
| 93 | 2-naphthyl | α,α,α-trifluoro-m-toluyl | 2,2-diphenylethyl |
| 93 | 2-naphthyl | α,α,α-trifluoro-m-toluyl | pent-3-yl |
| 93 | 2,4-dichlorophenyl | α,α,α-trifluoro-m-toluyl | 2,2-diphenylethyl |
| 93 | 2-naphthyl | α,α,α-trifluoro-m-toluyl | diphenylmethyl |
| 93 | 2-naphthyl | α,α,α-trifluoro-m-toluyl | 2-furyl |
| 93 | 2-naphthyl | 2,4-difluorophenyl | (1-naphthyl)methyl |
| 92 | 2-naphthyl | 3-chlorophenyl | diphenylmethyl |
| 92 | 2-naphthyl | α,α,α-trifluoro-p-toluyl | 1-indanyl |
| 92 | 2-naphthyl | α,α,α-trifluoro-m-toluyl | 1-indanyl |
| 92 | α,α,α-trifluoro-p-toluyl | 4-chlorophenyl | 1,2,3,4-tetrahydronaphth-1-yl |
| 92 | 2,4-dichlorophenyl | 4-biphenylyl | 1,2,3,4-tetrahydronaphth-1-yl |
| 91 | 2-naphthyl | m-anisyl | phenethyl |
| 91 | phenyl | 2-fluorophenyl | 3-pyridinyl |
| 91 | 2,4-dichlorophenyl | 3,5-difluorophenyl | 3-pyzidinyl |
| 91 | 2-naphthyl | 2,4-dichlorophenyl | 3-pyridinyl |
| 91 | 2-naphthyl | α,α,α-trifluoro-p-toluyl | 3-benzylpentamethylenyl |
| 91 | 2-naphthyl | α,α,α-trifluoro-p-toluyl | 3-phenylpropyl |
| 91 | α,α,α-trifluoro-p-toluyl | α,α,α-trifluoro-p-toluyl | N-phenyl-2,2'-aminodiethyl |
| 91 | 2,4-dichlorophenyl | 4-biphenylyl | phenethyl |
| 90 | 2,4-dichlorophenyl | 4-biphenyyl | 1-indanyl |
| 90 | 2-naphthyl | 4-fluorophenyl | 2,2-diphenylethyl |
| 90 | α,α,α-trifluoro-p-totuyl | 3-(phenoxy)phenyl | 1,2,3,4-tetrahydronaphth-1-yl |
| 90 | 2-napbthyl | α,α,α-trifluoro-m-toluyl | 1,2,3,4-tetrahydronaphth-1-yl |
| 90 | 2,4-dichlorophenyl | α,α,α-trifluoro-p-toluyl | N-(α,α,α-trifluoro-m-toluyl)-2,2'-aminodiethyl |
| 90 | p-toluyl | 2-chlorophenyl | (1-naphthyl)methyl |
| 90 | α,α,α-trifluoro-p-toluyl | 3-(phenoxy)phenyl | N-phenyl-2,2'-aminodiethyl |
| 90 | 2,4-dichlorophenyl | 4-biphenylyl | (1-naphthyl)methyl |
| 90 | 2,4-dichlorophenyl | α,α,α-trifluoro-m-toluyl | 1,2,3,4-tetrahydronaphth-1-yl |

Examination of these highly active molecules revealed that the first 25 molecules exhibit 94% inhibition or better. Of these molecules, 12 draw all three structural diversity elements from the aforementioned sets, 9 draw two of these structural diversity elements and the others draw one.

What is claimed is:

1. An n×m×p array of different chemical compounds each having the following scaffold structure:

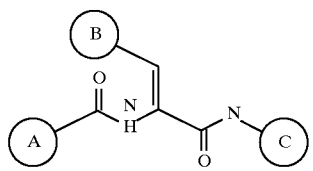

wherein n, m and p are integers, A, B and C are diversity elements and at least one of A, B, or C is one of the following moieties:

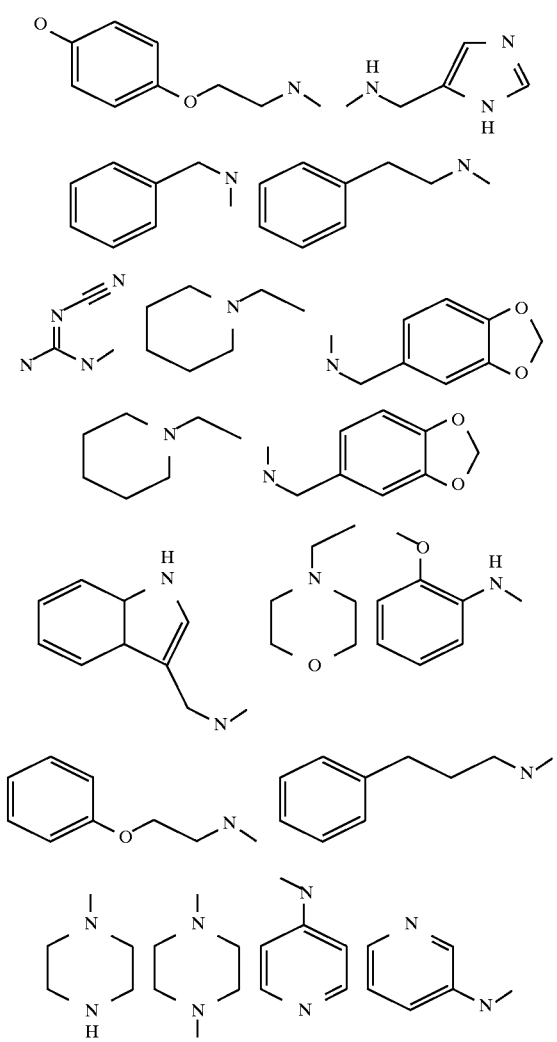

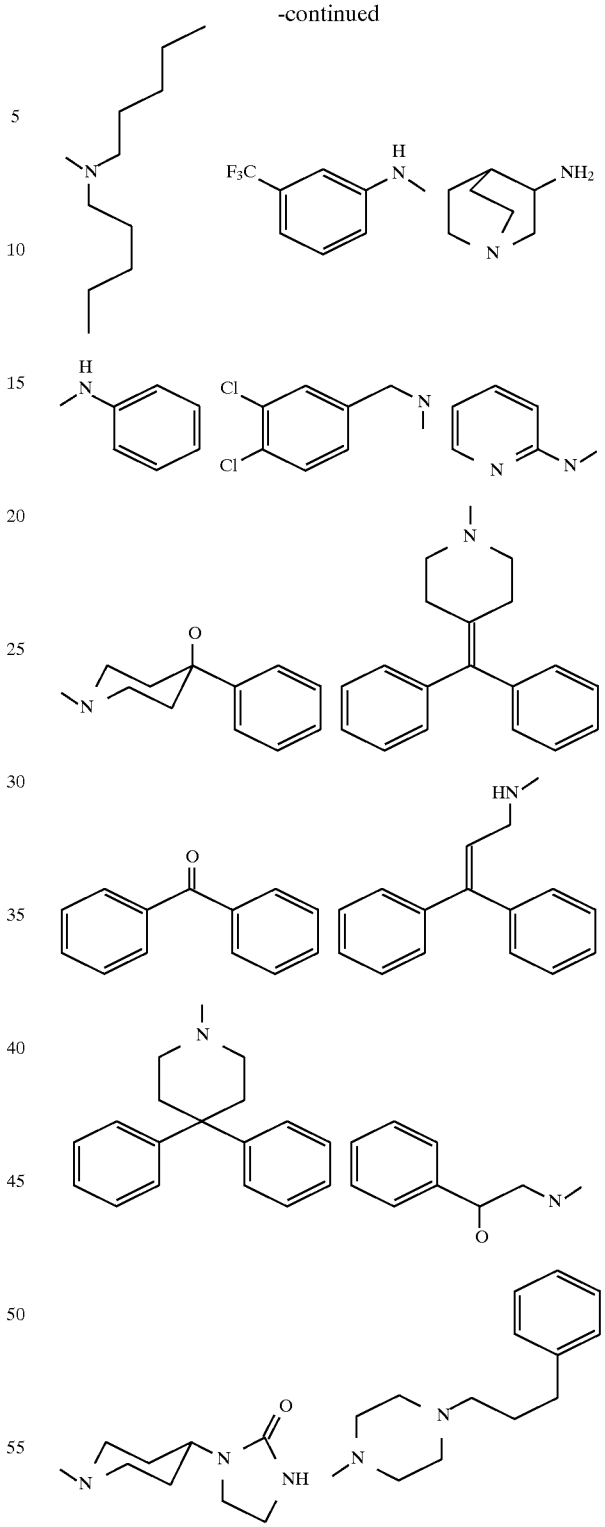

2. The array of claim 1 wherein $n \geq 5$, $m \geq 2$ and $p \geq 1$.

3. The array of claim 1 wherein the product of n, m and p is $\geq 25$.

4. The array of claim 1 wherein $n \geq 8$, $m \geq 12$ and $p \geq 2$.

5. An n×m×p array of different chemical compounds having the following scaffold structure:

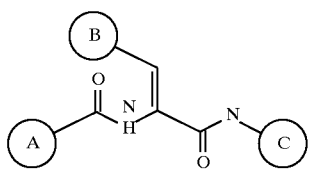

wherein n is 8, m is 32 and p is 40 and

"A" is phenyl, m-methoxyphenyl, 2-naphthyl, 2-thiophenyl, α,α,α-trifluoro-p-toluyl, 2,4-dichlorophenyl, p-toluyl, or m-toluyl;

"B" is 2,4-difluorophenyl, 2-fluorophenyl, 3-fluorophenyl, 4-fluorophenyl, α,α,α-trifluoro-m-toluyl, α,α,α-trifluoro-p-toluyl, o-toluyl, m-toluyl, p-toluyl, 4-ethylphenyl, phenyl, 4-biphenylyl, 1-naphthyl, 4-(trifluoromethoxy)phenyl, 3-(phenoxy)phenyl, 2-thiophenyl, 3-thiophenyl, 3,5-difluorophenyl, 3-pyridinyl, 4-pyridinyl, 4-chlorophenyl, 3-quinolinyl, 4-quinolinyl, 2-furyl, 3-furyl, or 5-methylfur-2-yl; and "C" is (2-tetrahydrofuryl)methyl, isobutyl, (+)-sec-butyl, cyclobutyl, cyclohexyl, 1-ethylpropyl, 2-hydroxyethyl, (+)-hydroxypropyl, 2-hydroxyphenethyl, (−)-ephidryl, 1-hydroxy-4-methylpent-2-yl, pentamethylenyl, 3-benzylpentamethylenyl, 2,2'-bis-ethylether, 4-phenylbut-2-yl, 3-phenylpropyl, benzyl, phenethyl, 1,2,3,4-terahydronaphthyl, 2-(p-toluyl)ethyl, diphenylmethyl, 2,2-diphenylethyl, 1-indanyl, 2-phenethyl, (1-naphthyl)methyl, (2-furyl)methyl, 3,4-dimethoxyphenethyl, N-ethylcarboxy-2,2'-aminodiethyl, 2-(N-pyrrolidinyl)ethyl, N-phenyl-2,2'-aminodiethyl, 1-benzyl-4-piperidinyl, N-piperonyl-2,2'-aminodiethyl, 3-(4-morpholinyl)propyl, 3(1-imidazolyl)propyl, 3-(N,N-dimethylamino)propyl, N-(α,α,α-trifluoro-m-toluyl)-2,2'-aminodiethyl, (2-pyridinyl)methyl, 2-(1-piperidinyl)ethyl, or N-methyl-2,2'-aminodiethyl.

6. The array of claim 1 wherein each compound is different.

7. A compound from the array of claim 1.

8. A compound from the array of claim 5.

9. A compound comprising the scaffold:

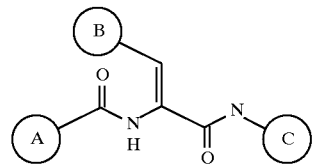

wherein A, B, and C are diversity elements, and one of the following combinations of diversity elements:

| A | B | C |
|---|---|---|
| 2,4-dichlorophenyl | phenyl | cyclohexyl |
| 2-naphthyl | α,α,α-trifluoro-m-toluyl | 1,2,3,4-tetrahydronaphth-1-yl |
| 2-naphthyl | α,α,α-trifluoro-m-toluyl | diphenylmethyl |
| 2,4-dichlorophenyl | α,α,α-trifluoro-m-toluyl | diphenylmethyl |
| 2-naphthyl | α,α,α-trifluoro-m-toluyl | 2-(p-toluyl)ethyl |
| 2-naphthyl | α,α,α-trifluoro-p-toluyl | diphenylmethyl |
| p-toluyl | 2,4-difluorophenyl | 2-hydroxyphenethyl |
| 2-naphthyl | 3-quinolinyl | (1-naphthyl)methyl |
| 2-naphthyl | α,α,α-trifluoro-p-toluyl | 4-phenylbut-2-yl |
| 2,4-dichlorophenyl | 4-biphenylyl | diphenylmethyl |
| 2-naphthyl | 4-(trifluoromethoxy)phenyl | diphenylmethyl |
| 2-naphthyl | α,α,α-trifluoro-p-toluyl | 2,2-diphenylethyl |
| 2-naphthyl | α,α,α-trifluoro-p-toluyl | 1,2,3,4-tetrahydronaphth-1-yl |
| 2,4-dichlorophenyl | 3-(phenoxy)phenyl | 2-(p-toluyl)ethyl |
| p-toluyl | 2-chlorophenyl | 3-(4-morpholinyl)propyl |
| 2-naphthyl | 2,4-dichlorophenyl | 2-hydroxyphenethyl |
| 2-naphthyl | α,α,α-trifluoro-m-toluyl | 3-benzylpentamethylenyl |
| α,α,α-trifluoro-p-toluyl | α,α,α-trifluoro-p-toluyl | 2-(p-toluyl)ethyl |
| α,α,α-trifluoro-p-toluyl | α,α,α-trifluoro-p-toluyl | 1,2,3,4-tetrahydronaphth-1-yl |
| α,α,α-trifluoro-p-toluyl | 3-(phenoxy)phenyl | diphenylmethyl |
| 2,4-dichlorophenyl | 4-biphenylyl | 2-(p-toluyl)ethyl |
| 2-naphthyl | m-anisyl | diphenylmethyl |
| 2-naphthyl | α,α,α-trifluoro-m-toluyl | (1-naphthyl)methyl |
| 2,4-dichlorophenyl | 4-biphenylyl | benzyl |
| 2,4-dichlorophenyl | 3,5-difluorophenyl | 2,2-diphenylethyl |
| 2-naphthyl | α,α,α-trifluoro-m-toluyl | 1-hydroxy-4-methylpent-2-yl |
| 2-naphthyl | 4-(trifluoromethoxy)phenyl | 1,2,3,4-tetrahydronaphth-1-yl |
| 2-naphthyl | α,α,α-trifluoro-m-toluyl | 2,2-diphenylethyl |
| 2-naphthyl | α,α,α-trifluoro-m-toluyl | pent-3-yl |
| 2,4-dichlorophenyl | α,α,α-trifluoro-m-toluyl | 2,2-diphenylethyl |
| 2-naphthyl | α,α,α-trifluoro-m-toluyl | diphenylmethyl |
| 2-naphthyl | α,α,α-trifluoro-m-toluyl | 2-furyl |
| 2-naphthyl | 2,4-difluorophenyl | (1-naphthyl)methyl |
| 2-naphthyl | 3-chlorophenyl | diphenylmethyl |
| 2-naphthyl | α,α,α-trifluoro-p-toluyl | 1-indanyl |
| 2-naphthyl | α,α,α-trifluoro-m-toluyl | 1-indanyl |
| α,α,α-trifluoro-p-toluyl | 4-chlorophenyl | 1,2,3,4-tetrahydronaphth-1-yl |
| 2,4-dichlorophenyl | 4-biphenylyl | 1,2,3,4-tetrahydronaphth-1-yl |
| 2-naphthyl | m-anisyl | phenethyl |
| phenyl | 2-fluorophenyl | 3-pyridinyl |
| 2,4-dichlorophenyl | 3,5-difluorophenyl | 3-pyridinyl |
| 2-naphthyl | 2,4-dichlorophenyl | 3-pyridinyl |
| 2-naphthyl | α,α,α-trifluoro-p-toluyl | 3-benzylpentamethylenyl |

-continued

| A | B | C |
| --- | --- | --- |
| 2-naphthyl | α,α,α-trifluoro-p-toluyl | 3-phenylpropyl |
| α,α,α-trifluoro-p-toluyl | α,α,α-trifluoro-p-toluyl | N-phenyl-2,2'-aminodiethyl |
| 2,4-dichlorophenyl | 4-biphenylyl | phenethyl |
| 2,4-dichlorophenyl | 4-biphenylyl | 1-indanyl |
| 2-naphthyl | 4-fluorophenyl | 2,2-diphenylethyl |
| α,α,α-trifluoro-p-toluyl | 3-(phenoxy)phenyl | 1,2,3,4-tetrahydronaphth-1-yl |
| 2-naphthyl | α,α,α-trifluoro-m-toluyl | 1,2,3,4-tetrahydronaphth-1-yl |
| 2,4-dichlorophenyl | α,α,α-trifluoro-p-toluyl | N-(α,α,α-trifluoro-m-toluyl)-2,2'-aminodiethyl |
| p-toluyl | 2-chlorophenyl | (1-naphthyl)methyl |
| α,α,α-trifluoro-p-toluyl | 3-(phenoxy)phenyl | N-phenyl-2,2'-aminodiethyl |
| 2,4-dichlorophenyl | 4-biphenylyl | (1-naphthyl)methyl |
| 2,4-dichlorophenyl | α,α,α-trifluoro-m-toluyl | 1,2,3,4-tetrahydronaphth-1-yl |

\* \* \* \* \*